United States Patent [19]

Weiner

[11] Patent Number: 4,912,329
[45] Date of Patent: Mar. 27, 1990

[54] PORTABLE BATTERY-OPERATED AMBIENT AIR ANALYZER

[75] Inventor: Seymour Weiner, Stamford, Conn.
[73] Assignee: The Foxboro Company, Foxboro, Mass.
[21] Appl. No.: 331,452
[22] Filed: Mar. 31, 1989

Related U.S. Application Data

[62] Division of Ser. No. 32,038, Mar. 30, 1987, Pat. No. 4,818,875.
[51] Int. Cl.⁴ ............................................. G01N 21/35
[52] U.S. Cl. .................... 250/343; 250/493.1
[58] Field of Search ............ 250/504 R, 504 H, 493.1, 250/343

[56] References Cited

U.S. PATENT DOCUMENTS

| | | | |
|---|---|---|---|
| 3,904,880 | 9/1975 | Benz et al. | 250/343 |
| 4,437,005 | 3/1984 | Ophoff et al. | 250/343 |
| 4,560,875 | 12/1985 | Crowder | 250/343 |

FOREIGN PATENT DOCUMENTS 7805821 12/1978 Netherlands ..................... 250/493.1

Primary Examiner—Carolyn E. Fields
Attorney, Agent, or Firm—Parmelee, Bollinger & Bramblett

[57] ABSTRACT

Portable battery-operated ambient air analyzer comprising an electrically-energized incandescent source of infra-red radiation producing a beam passing through an air sample to a sensor. The infra-red source is surrounded by an explosion-proof enclosure to prevent an explosion internally of the enclosure being propagated out to the atmosphere. The incandescent source is a self-supporting filamentary coil having no interior core or mandrel. The coil is formed of a metal composition including aluminum, chromium and iron, operated at a temperature of less than 1000° C.

2 Claims, 2 Drawing Sheets

PORTABLE BATTERY-OPERATED AMBIENT AIR ANALYZER

This application is a divisional of application Ser. No. 032,038 as filed on Mar. 30, 1987, now U.S. Pat. No. 4,818,875.

BACKGROUND OF THE INVENTION

1. Field of the Invention

This invention relates to infra-red spectrometers of the multi-wavelength type. More particularly, this invention relates to portable, battery-operated spectrometers used for ambient air analysis.

2. Description of the Prior Art

Portable battery-operated ambient air analyzers have been employed for a number years to determine the concentration of a wide variety of gases and vapors. Such devices typically comprise a hand-held or shoulder-strap-supported housing containing an infra-red source producing a single beam of radiation. This beam is selectively filtered in accordance with the gas to be measured, and is directed through an air sample drawn into a gas cell by an internal sampling pump. The beam emerging from the gas cell is detected by a sensor to produce a signal which is operated on, e.g. by a microprocessor, to develop a concentration measurement for display to the person carrying the analyzer. U.S. Pat. No. 3,877,812 discloses important aspects of one such ambient air analyzer which has been highly successful commercially.

Although such prior art devices have found widespread application, their use has not been permitted in sites such as many kinds of hazardous waste sites which contain potentially inflammable or explosive components. For such more dangerous sites, it has been the usual practice simply to capture an air sample at the site, as in a sealed container, and convey it manually or by vehicle to a remote place for analysis by a non-portable analyzer. Alternatively, for dangerous sites where frequent or continuous monitoring is required, a permanent sampling system may be installed to continuously draw sample gas from the site and transmit it, as through a sealed tube, to an adjacent laboratory for analysis. The analytical equipment used at such laboratory typically will include elaborate isolation provisions and other safety features to prevent damage from explosions or the like of flammable gases which might be drawn in from the site being monitored. Because of such safety provisions, the equipment is necessarily bulky and expensive to manufacture.

It has been found that the prior art techniques for monitoring the air at sites where flammable or explosive mixtures might be present are unsatisfactory, primarily due to high cost and complexity. These difficulties tend to inhibit the monitoring at sites where analysis for toxic gases is very desirable, for example at workplace environments or hazardous waste sites where due to the presence of workers it is vital to know of the existence and the amount of any toxic gases. Thus, it has become very important to provide improved apparatus for monitoring the ambient air at such sites where flammable or explosive gases or vapors may be present.

SUMMARY OF THE INVENTION

In a preferred embodiment of the invention, to be described hereinbelow in detail, there is provided a portable, battery-operated ambient air analyzer suited for operation at sites where flammable or explosive gas or vapors may be present. This instrument includes, in common with conventional prior art portable analyzers, an electrically-energized incandescent source of infra-red radiation producing a radiant beam which passes through an air sample in a gas cell and is directed to a sensor which together with an associated microprocessor calculates absorbance values to produce measurements for display to the person carrying the instrument. Unlike prior art portable analyzers, the infra-red source of this instrument is contained within an enclosure so arranged as to be explosion-proof, as that term is known and defined in the art. In more specific detail, the enclosure for the infra-red source, although not hermetically sealed, is so arranged that any flame path to outside atmosphere for an explosion within the enclosure is appropriately long and has a sufficiently narrow gap (i.e. the spacing between elements adjacent the flame path) as to assure sufficient cooling of escaping flame gas to prevent the emerging gases from initiating a further explosion in the ambient atmosphere surrounding the instrument. Moreover, the enclosure is so designed as to prevent any separate elements of the structure from being blown outwardly by the force of an internal explosion. Thus, the portable ambient air analyzer instrument of this invention is well suited to make measurements of gas concentrations at sites where flammable or explosive gas might be present.

Accordingly, it is an object of this invention to provide improved ambient air analysis apparatus for use at sites where flammable or explosive gases may be present. Other objects, aspects and advantages of the invention will in part be pointed out in, and in part apparent from, the following description of a preferred embodiment of the invention, considered together with the accompanying drawings.

DESCRIPTION OF THE PREFERRED EMBODIMENT

Figure 1:
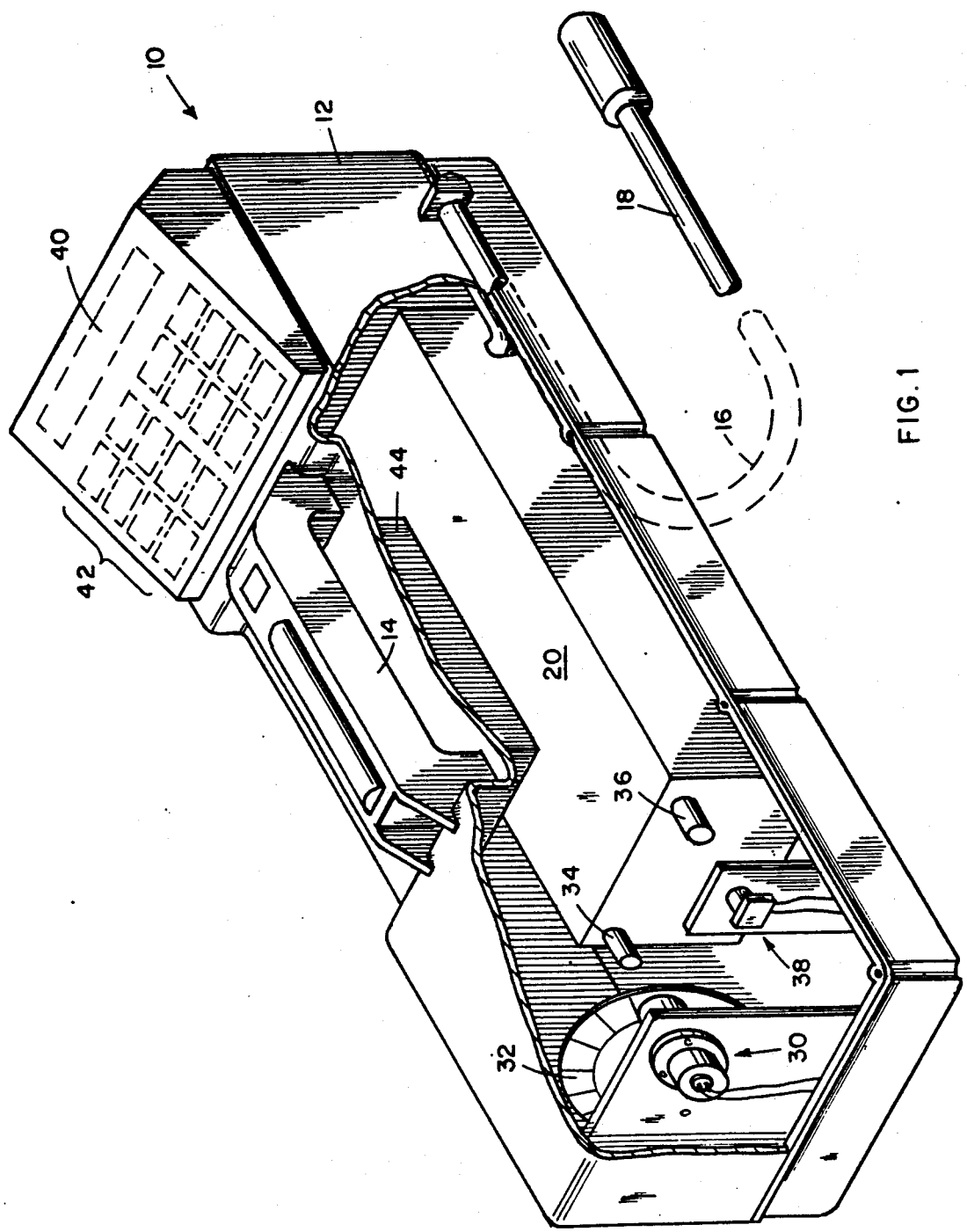
FIG. 1 is a perspective view, partly broken away, showing a portable, battery-operated ambient air analyzer in accordance with this invention.

Referring first to FIG. 1, the ambient air analyzer instrument in accordance with this invention is generally indicated at 10 and comprises an outer housing 12 of generally rectangular box-like shape. This housing is formed with a handle indicated at 14 to permit a person to hand-carry the instrument while performing an analysis of ambient air. The instrument includes a flexible hose 16 having at one end a wand 18 to be held by the operator in a region where a gas sample is to be taken. The sample is drawn in through the wand and the hose 16 by an internal sampling pump (not shown) to a gas cell 20 of known construction.

At the left-hand end of the housing 12 is a source of infra-red radiation generally indicated at 30, and to be described in more detail hereinbelow. This source produces a beam of infra-red radiation, e.g. covering at least the wavelength range of 2.5 to 14.5 μm. This beam is directed to a circular variable filter 32 having a number of peripheral segments which can be controllably positioned in the path of the infra-red beam, in known fashion. The beam emerging from this filter is directed (as by means of a light pipe, not shown) to an entrance schematically illustrated at 34 at the near end of the gas cell 20. Inside this gas cell, the infra-red beam traverses the gas sample in a manner to provide a path length appropriate to the analysis desired.

The infra-red beam emerges from the gas cell 20 at an exit schematically illustrated at 36 and is directed (by means not shown) to a sensor schematically illustrated at 38 This sensor produces an output signal responsive to the absorbance of the beam in passing through the gas sample, and this output signal is transmitted to a microprocessor (not shown) which makes calculations appropriate to the selected gas component so as to develop a measurement of the concentration of that gas. This measurement is presented to the operator by means of an LCD display generally indicated at 40, in concentration/absorbance units. Adjacent the LCD display 40 is a keyboard 42 to permit the operator to control the microprocessor, e.g. to select the functional mode of the instrument, and to program the analyzer for any one of a large number of gases which can be measured by the instrument.

All of the electrical power for operation of the ambient air analyzer instrument 10 is furnished by an internal battery pack 44. Preferably, this battery pack is rechargeable. External battery packs also can be provided to extend the operating time as needed. Low battery or sample loss flow conditions can be presented on the LCD display 40.

Figure 2:
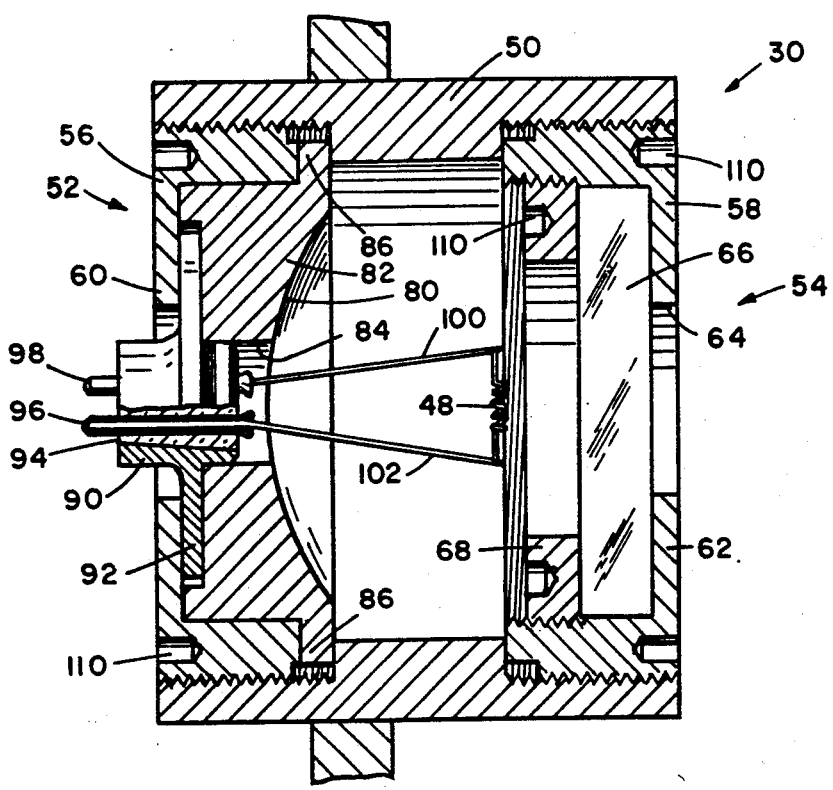
FIG. 2 is a vertical section through the center of the infra-red source of the instrument shown in FIG. 1.
Figure 3:
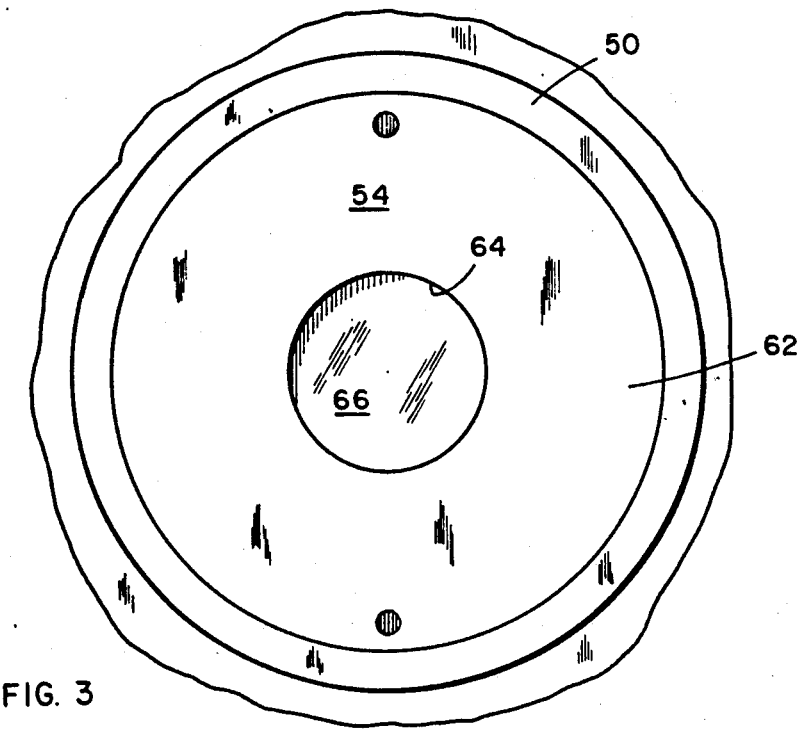
FIG. 3 is an elevation view of the source of FIG. 2, as seen from the right-hand side of FIG. 2.

Referring now to FIG. 2, the source 30 comprises a filamentary coil 48 which is fully surrounded by a substantially-sealed (but not hermetically-sealed) enclosure. This enclosure includes a tubular central casing member 50 of cylindrical shape (see also FIG. 3), the ends of which are closed off by end caps 52, 54. These end caps have tubular (cylindrical) side walls 56, 58 threadedly engaged with the interior surface of the central casing member 50, and integral end plates 60, 62 perpendicular to the axis of the cylindrically-shaped central casing member 50.

The right-hand end plate 62 is formed with a centered opening 64 behind which is secured an infra-red window 66, e.g. formed of a translucent compound such as zinc selenide adapted to pass infra-red radiation. A locking ring 68 is threadedly engaged with the interior of the end cap 54, and presses against the left-hand surface of the window 66 to hold the window firmly against the end plate 62.

The coil 48 when energized by flow of electrical current becomes incandescent and produces radiation including the infra-red wavelengths. Much of the radiation going to the left of this coil strikes a polished spherical mirror 80 and is reflected thereby back towards the opening 64 to augment the radiation going through that opening directly from the coil. The reflected radiation preferably is focussed at the plane of the circular variable filter 32 (shown in FIG. 1), from whence it is directed to the gas cell 20 as previously described.

The mirror 80 is formed as part of a mirror holder 82 having a central aperture 84. Fitted into this aperture is a metal lead support member 90 having a ring-shaped flange 92 which is gripped between the mirror holder 82 and the end plate 60 of the end cap 52. The lead support member 90 also is formed with a central aperture which receives a glass plug 94 fused to the metal of the support member. Molded into this glass plug are a pair of metal tubes 96, 98 carrying electrical leads, 100, 102 which extend rigidly in side-by-side fashion as support elements for the coil 48 in the interior of the enclosure.

The ends of the filamentary coil 48 are secured to these lead extensions 100, 102, as by spot welding, and the coil structure is self-supporting. That is, the coil is not provided with the usual ceramic mandrel or core which in prior art devices the coil was wrapped about, and which in turn was secured to the lead extensions. It has been found that this change has reduced the electrical power requirements of the coil 48 by approximately one-half, for the same radiation intensity, apparently because there now is no heat loss which previously occurred by conduction through the ceramic core and radiation from the core. This reduction is a very important benefit in a battery-operated instrument, because it increases the length of time which the equipment may be used before needing a battery replacement.

The structure of the source 30 has been so arranged that the unit as a whole is explosion-proof (sometimes also referred to as intrinsically safe). In the United States, and a number of other countries, determining and certifying the explosion-proof capability of a device is the responsibility of certain publicly-accessible institutions or agencies. These agencies will upon request analyze the design of a proposed structure and, if it is satisfactory, certify it as explosion-proof in accordance with pre-established and generally recognized technical requirements. One such agency, in the U.S., is known as Factory Mutual Research Corporation (referred to in short as FM). The design of the source 30 as shown herein has been examined by that agency and certified as explosion-proof. Certain features of the source design are particularly important to such certification, as will be explained hereinbelow.

Referring again to FIG. 2, it will be seen that the end plate 62 overlies the window 66 for a substantial distance radially, i.e. in from the outer periphery of the window. Moreover, the adjoining parallel surfaces of these two elements are specially formed to be flat and smooth. The structural dimensions are so set that any potential flame path from an internal explosion to the outside atmosphere which includes this radial route between the end plate 62 and the window 66 will have a length and gap spacing meeting requirements of FM for a device of the internal volume of the source 30. (These requirements for the source 30 employed in the preferred commercial embodiment described herein are: a path length of 0.38" and a flatness for adjoining surfaces of less than 250 microinches.)

The end cap 54 also serves to hold the window 66 captive, i.e. so as to prevent the window from being expelled from the interior of the enclosure in the event of an explosion in the enclosure. This restraint is provided by the end plate 62 which in turn is held in position by the threaded engagement between the tubular side wall 58 of the end cap and the central casing member 50. It may also be noted that this threaded engagement between these two members provides an alternative flame path to the outside of the enclosure, but the length of that path (that is, the number of threads) is made sufficiently large that any escaping gases would be sufficiently cool to prevent an explosion from being transmitted to outside atmosphere.

Referring now to the left-hand end of the central casing member 50, it will be seen that the lead support member 90 is arranged with respect to the end cap 52 somewhat as the window 66 is arranged with respect to the right-hand end cap 54. That is, the left-hand end plate 60 overlies the ring-shaped flange 92 of the lead support member for a substantial distance radially and the adjoining surfaces are formed to be flat and smooth, so as to meet the appropriate requirements for the length of the potential flame path and the necessary close gap spacing between the adjoining elements establishing such flame path. Moreover, the overlying portion of the end plate 60 serves to restrain the lead support member 90 in the event of an internal explosion, thus helping to prevent it from being expelled from the enclosure in that event. The mirror holder 82 also is formed with a circular peripheral flange 86 which is engaged by the end cap 52 to assure that the mirror holder will not be expelled from the enclosure by the force of an internal explosion in the enclosure.

The alternative potential flame path formed by the threaded engagement between the end cap and the central casing member 50 is sufficiently long (by having the necessary number of threads) to assure that an internal explosion will not be transmitted by that route to the outside at a high enough temperature to continue or renew the explosion in the outside atmosphere.

The glass plug 94 in the lead support member 90 is formed with a slight taper (shown somewhat exaggeratedly) along its central axis to assure that this plug will not be ejected from the enclosure in the event of an internal explosion. Similarly, the lead tubes 96, 98 are formed at their inner ends with flared tips to prevent these lead tubes from being expelled from the enclosure through the glass plug in the event of an internal explosion.

Incandescent coils used in prior art spectrometers frequently have been formed of nichrome. However, it has been found that nichrome vaporizes, and in a substantially sealed enclosure will coat the interior surfaces, ultimately rendering the source inoperable. This problem has been solved by forming the coil 48 from a metal comprising aluminum, chromium and iron, preferably 5.5% aluminum, 22% chromium, and the balance iron. Such a material is available commercially under the name "Kanthal A-1", for electric resistance and high temperature alloys. The supplier of that material recommends an operating temperature of 1375° C., but some vaporization occurs at that temperature; it has been found that operation should be at a temperature below 1000° C., preferably 925° C.

Cements may be employed with advantage between adjacent surfaces of some of the elements of the source 30. For example, cement may be applied to both sides of the flange 92 of the lead support member 90. No cement is used between the window 66 and the end plate 62, but a lubricant may be applied between the locking ring 68 and the window. The outer curved surface of the window is dimensioned to provide a close fit within the end cap 54, but that surface is not specially polished for smoothness (and small gap spacing) as is the flat side surface of the window adjoining the end plate 62. The length of the potential flame path along the side of the glass plug 94 is sufficient to assure good gas cooling in the event of an internal explosion (i.e. the length is greater than 0.38"), and the fused glass/metal surfaces provide a close and intimate engagement. Principal components of the source 30 such as the casing 50 and the end caps 52, 54 preferably are made of aluminum. Small drill holes are formed in several of the elements, e.g. as shown at 110, to provide for assembly and disassembly of the enclosure only by special tools having projections matching those drill holes. Set screws are provided at appropriate places to further insure that the source remains in assembled condition unless purposely disassembled.

Although a specific preferred embodiment of this invention has been described hereinabove in detail, it is desired to emphasize that this has been for the purpose of illustrating the invention, and should not be considered as necessarily limitative of the invention, it being understood that many modifications can be made by those skilled in the art while still practicing the invention claimed herein.

What is claimed is:

1. In operating a portable ambient air analyzer instrument of the type having an outer housing with means permitting the instrument to be carried by a person onto a site where gases exist and require measurement of the concentration thereof, said analyzer including an electrically-energized incandescent source supplied with a flow of electrical current to produce a corresponding beam of infra-red radiation passing through a gas cell containing a gas sample and being directed thereafter to a sensor for analysis so as to produce measurements to be displayed, a battery in said housing to supply all of the electrical power required for the operation of said instrument including said flow of electrical current to said incandescent source; said incandescent source of infra-red radiation comprising an electrically energized coil formed as a composite of aluminum, chromium and iron; and an enclosure surrounding and substantially sealing said incandescent source of infra-red radiation while permitting transmission of said infra-red radiation through a window in said enclosure, said enclosure further including means providing for explosion-proof operation of said source;

the improved method wherein said coil of aluminum, chromium and iron is operated at a temperature less than 1000° C., thereby avoiding harmful vaporization build-up of metal and/or oxide on the interior surfaces of said enclosure so as to assure achieving effective radiation intensity through said window.

2. The method of claim 1, wherein said coil is operated at a temperature of approximately 925° C.

* * * * *